United States Patent [19]
Prichard

[11] Patent Number: 5,988,700
[45] Date of Patent: Nov. 23, 1999

[54] LEAK PROOF TUBE CONNECTION SITE

[75] Inventor: James B. Prichard, St. Peters, Mo.

[73] Assignee: Sherwood Services A G, Schaffhausen, Switzerland

[21] Appl. No.: 08/766,534

[22] Filed: Dec. 11, 1996

Related U.S. Application Data

[60] Provisional application No. 60/008,580, Dec. 13, 1995.

[51] Int. Cl.$^6$ .................................................. A61M 25/14
[52] U.S. Cl. ......................... 285/148.23; 285/8; 138/118; 604/905
[58] Field of Search ...................... 285/148.23, FOR 159, 285/148.18, 332, 334.2, 423, 8, 107; 684/283, 905; D23/266; 138/109, 118, 172

[56] References Cited

U.S. PATENT DOCUMENTS

| | | | |
|---|---|---|---|
| D. 297,759 | 9/1988 | Kerschke | D23/266 |
| 2,025,067 | 12/1935 | Miller | 285/148.23 |
| 2,186,987 | 2/1940 | Kellems | 138/118 X |
| 2,788,231 | 4/1957 | Crow | 285/8 X |
| 5,047,021 | 9/1991 | Utterberg | 285/332 X |
| 5,066,286 | 11/1991 | Ryan | 604/240 |
| 5,242,389 | 9/1993 | Schrader et al. | 604/54 |
| 5,267,983 | 12/1993 | Ollschlager et al. | 604/283 |
| 5,284,475 | 2/1994 | Mackal | 604/283 X |
| 5,399,173 | 3/1995 | Parks et al. | 285/148.23 X |
| 5,620,427 | 4/1997 | Werschmidt et al. | 604/283 |
| 5,688,254 | 11/1997 | Lopez et al. | 604/283 |

FOREIGN PATENT DOCUMENTS

| 21415 | of 1902 | United Kingdom | 285/332 |
|---|---|---|---|

OTHER PUBLICATIONS

EngineersEXPRESS, Inc., Catalog, Thomas Register of American Manufacturers, 86th ed., vol. 25, Thomas Publishing Co., New York, pp. 4087, 4092, 4093, 4097–4102, 1996.

Shigley et al, Mechanical Engineering Design, McGraw–Hill, New York, pp. 22 and 798, 1983.

*Primary Examiner*—Lynne H. Browne
*Assistant Examiner*—Greg Binda
*Attorney, Agent, or Firm*—Mark S. Leonardo; Brown, Rudnick, Freed & Gesmer

[57] ABSTRACT

A fluidic connector with a leak proof connection site that includes a first larger diameter portion, a second smaller diameter portion and a deformable buckling region that forms a part of both the first and second diameter portions where the two portions join. The first larger diameter portion forms a separate inner surface for receiving a plug to securely seal off the connection site from fluid communication therethrough while the second smaller diameter portion is adapted to receive and securely seal different sizes of male adapters used for attaching a lumen. The deformable buckling region forms a structural buffer between the first and second diameter portions in order to maintain the diameter of the first larger diameter portion when the second smaller diameter portion is stretched out by prolonged insertion of a nonconforming male adaptor. In addition, an adapter is provided which permits flexibility in use and provides a redundant fluid seal, without exhibiting creep.

24 Claims, 7 Drawing Sheets

1

LEAK PROOF TUBE CONNECTION SITE

This application claims priority based on Provisional application Ser. No. 60/008,580 filed Dec. 13, 1995.

FIELD OF THE INVENTION

This invention relates generally to fluidic connectors. Specifically, the present invention relates to a leak proof connection site for fluidic connectors that is adapted to receive different size male adapters for connection to a tube. More particularly, the present invention relates to a leak proof connection site that utilizes different sealing surfaces for capping the connection site and securely sealing the male adapter therein without any attendant stretching or leaking of the connection site.

PRIOR ART

Fluidic connectors, such as Y-site connectors and single connectors, are well known in the art and a variety of different designs have heretofore been proposed to satisfy the objectives of various applications. For example, fluidic connectors are used in enteral feeding systems where the fluidic connector acts as a connection site between the feeding tube lumen and the tube assembly leading to a patient and ensures uninterrupted fluid communication between the feeding system and the patient during operation.

A typical fluidic connector comprises a proximal end connection site for fluid supply or withdrawal and a distal end connection site for attachment to a lumen leading to a patient. When the lumens leading to the proximal and distal end connection sites are connected thereto, the lumens are in closed fluid communication. The proximal end connection site is typically a "female" connection site with a hollow inner portion. This hollow inner portion accommodates a "male" adapter, through an interference fit, and provides fluid communication with the patient lumen. Further, the proximal end connection site usually incorporates a closure means where a plug tethered to the proximal end connection site is inserted into the hollow portion of the proximal end connection site in order to securely seal the lumen from fluid communication therethrough.

A fluidic connector with distal and proximal end connection sites designed to receive a lumen which can alternatively be plugged by a cap tethered to the connector is described in U.S. Pat. No. 5,242,389 to Schrader et al, the entire disclosure of which is hereby incorporated by reference. Schrader et al describes a fluidic connector with a proximal end connection site that has an inner surface adapted to receive both a male adapter for facilitating attachment to a lumen as well as a plug for closing off the connection site when the lumen is detached. However, using the same inner surface at the connection site to receive the male adapter and the plug can cause the connection site to suffer from a phenomenon, called permanent set or plastic deformation (and is synonomously known in the art as "creep").

The phenomenon referred to as plastic deformation can occur in one of two ways. First, if a non-conforming male adapter that is too large is inserted into the connection site, it can overstretch the connection site, thereby leading to a permanent deformation of the connection site. Secondly, a nonconforming male adapter that is left inserted into the connection site for a prolonged period can also lead to plastic deformation. Typically, this plastic deformation or stretching of the connection site occurs because different types of male adapters are commonly used in one type of fluidic connector with little or no conformity in size or design of the male adapter by vendors. Thus, a nonconforming male adapter is inserted into a proximal end connection site that is ill-suited in size to accommodate the adapter to the extent that the adapter begins to permanently stretch out the inner surface of the connection site over time clue to its nonconforming size. Further, this stretching of the connection site causes the connection site's inner surface to become unsuited for subsequent insertion of a plug because the plug no longer securely fits the stretched out connection site opening, thereby causing the connection site to leak fluid even when plugged.

Accordingly, creep is responsible for a loss of sealing function in the female when a non-conforming male adapter is inserted into the female receptacle for a prolonged period of time. Creep is also responsible for a loss of capping function because the part of the female responsible for capping is actually coupled to or part of the sealing surface.

U.S. Pat. No. 5,267,983 to Oilschlager et al used a tethered cap as a strap retainer to hold the male adapter together with the proximal connection site in order to ensure a secure fit with the adapter at all times. However, Oilschlager et al did not address the attendant problem of leaking due to stretching out of the connection site opening since both the capping and sealing surfaces were the same integral structure and the dimensional integrity of the capping surface could still be compromised when plastic deformation occurred.

Referring to FIG. 1, a prior art fluidic connector 1 is shown. The fluidic connector 1 comprises a wall 4 with patient connection site 2 at the distal end of connector 1 and a tube connection site 3 located at the proximal end of connector 1. The tube connection site 3 is adapted to receive a male adapter (not shown) for facilitating connection to a tubing assembly while the patient connection site 2 is adapted to connect to tubing leading to a patient.

The tube connection site 3 further includes an opening 5 which leads into a cavity 6 that is adapted to receive the male adapter. The cavity 6 includes a sealing and plugging portion 7 which extends from the opening 5 to the patient connection site 2 and is designed to form a secure interference fit with the male adapter when the adapter is inserted therein. The sealing and plugging portion 7 also serves as a plugging surface wherein a cap (not shown) is inserted through the opening 5 and engages a cap retaining groove 8 that closes off the opening 5 from fluid communication therethrough.

As of yet, nothing in the prior art has addressed the problem of developing a connection site for a fluidic connector that permits the use of various nonconforming male adapters to facilitate connection to a lumen without stretching out the inner surface of the connection site so that a plug will also securely fit thereto without leakage from the connection site.

To add complexity to the present situation, in Europe, reversed luer tapers are used for feeding tube connections. In other words, in Europe, the source has a female connection. The provision of a female connection by the source is the opposite from that used in intravenous connections. The reasoning employed by such the European system is that a female connection at source eliminates the possibility that a feeding source could be inadvertently connected to an intravenous cannula. Therefore, any universal fluidic connection solution to the creep problem would necessarily require some accommodation for the European system. Accordingly, there is not only a need in the art to develop a connection site for a fluidic connector that permits the use of non-conforming male adapters without creep, but there is also a need for one or more point-of-use adapters that would permit such a fluidic connector to be attached to any other type of connector, such as a male luer for the European market.

SUMMARY OF THE INVENTION

In brief summary, the present invention relates to a fluidic connector with an improved connection site that includes a first, larger diameter portion, a second, smaller diameter portion and a deformable buckling region that forms a part of both the first and second portions. The first, larger diameter portion forms a separate inner surface for receiving a plug to securely seal the connection site from fluid flow communication therethrough while the second, smaller diameter portion is adapted to receive and securely seal different sizes of male adapters for attaching a lumen. Finally, the deformable buckling region forms a structural buffer zone between the first and second portions that maintains the dimensions of the first, larger diameter portion when the second, smaller diameter portion is stretched out by the adapter due to short- or long-term insertion of the adapter therein.

Accordingly, a principal object of the present invention is to provide a fluidic connector having a first larger diameter portion whose dimensions and features will not be compromised when a second, smaller diameter portion is stretched out.

Another object of the present invention is to provide a fluidic connector with a connection site having two portions of different diameters that are structurally distinct from one another.

A further important object of the present invention is to provide a fluidic connector with smaller diameter portion that may accommodate different types and sizes of male adapters for insertion in an interference-type fit that minimizes the tendency for the connection site or the capping site to undergo plastic deformation and maximizes the axial retention force of the male adapter and cap.

Another object of the present invention is to provide a fluidic connector with a first, larger diameter portion that will not leak when a second, smaller diameter portion thereof is stretched out.

A further important object of the present invention is to provide a fluidic connector with a deformable buckling region as a buffer between the first and second diameter portions.

These and other objects of the present invention are realized in a presently preferred embodiment thereof, described by way of example and not necessarily by way of limitation, which provides for a fluidic connector with a connection site having two portions of different diameters. The first, larger diameter portion is designed to securely receive a plug without leakage caused by attendant stretching of the connection site by an nonconforming male adapter inserted therein and a second, smaller diameter portion is adapted for securely receiving a variety of male adapters. Finally, a deformable buckling region is provided as a buffer between the first and second diameter portions that maintains the shape and size of the larger diameter portion when the smaller diameter portion is stretched out.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION

Figure 2:
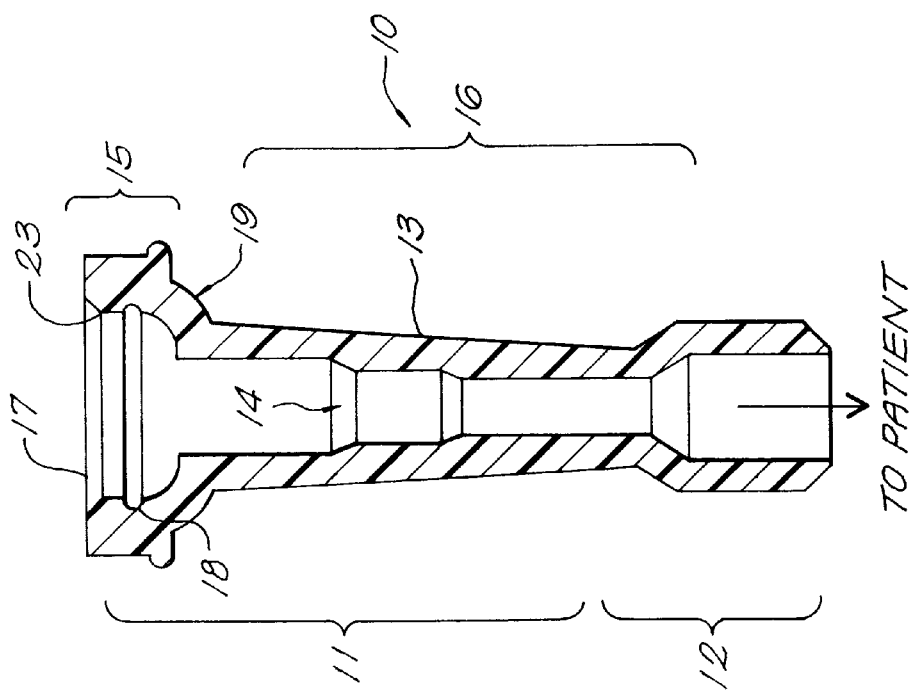
FIG. 2 shows a section view of a fluidic connector with a connection site formed in accordance with the present invention.
Figure 1:
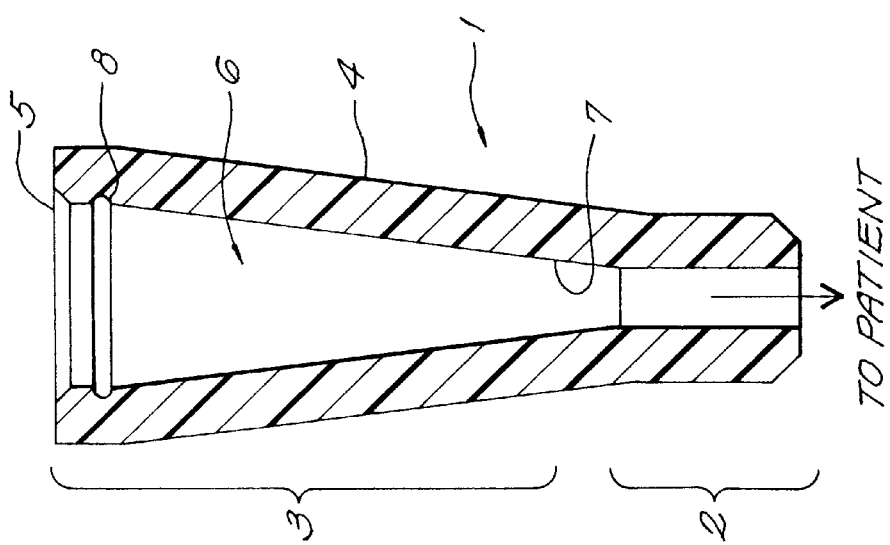
FIG. 1 shows a cross-section view of a fluidic connector with a prior art connection site.

Referring to FIG. 2, a fluidic connector 10 in accordance with the present invention will be discussed. The fluidic connector 10 comprises a tube connection site 11 at its proximal end and a patient connection site 12 at its distal end. The fluidic connector 10 further comprises a wall 13 that forms a hollow cavity 14 inside connector 10 that extends between both connection sites 11, 12 and permits fluid communication therethrough. The tube connection site 11 includes a first, larger diameter portion 15 and a second, smaller diameter portion 16. The first, larger diameter portion 15 provides an area for closing off the tube connection site 11 with a plug while the second, smaller diameter portion 16 provides a separate surface used for securely sealing, in an interference fit, a male adapter (not shown) when the adapter is inserted into the tube connection site 11.

The first, larger diameter portion 15 includes an opening 17 and a cap retaining groove 18 located below opening 17 for securely engaging the cap or plug upon insertion of a plug (not shown) into opening 17 therein. Although only one cap retaining groove 18 is shown, it is within the scope and spirit of the present invention that any suitable number of grooves 18 can be used to retain the cap. Further, the first, larger diameter portion 15 is of sufficient diameter to allow a tight fit for the cap, while permitting sufficient clearance between an inner surface 23 of portion 15 and the adapter when the adapter is inserted therein. Finally, the tube connection site 11 further includes a deformable buckling region 19 that forms a structural buffer zone between the first and second portions 15, 16.

Figure 3:
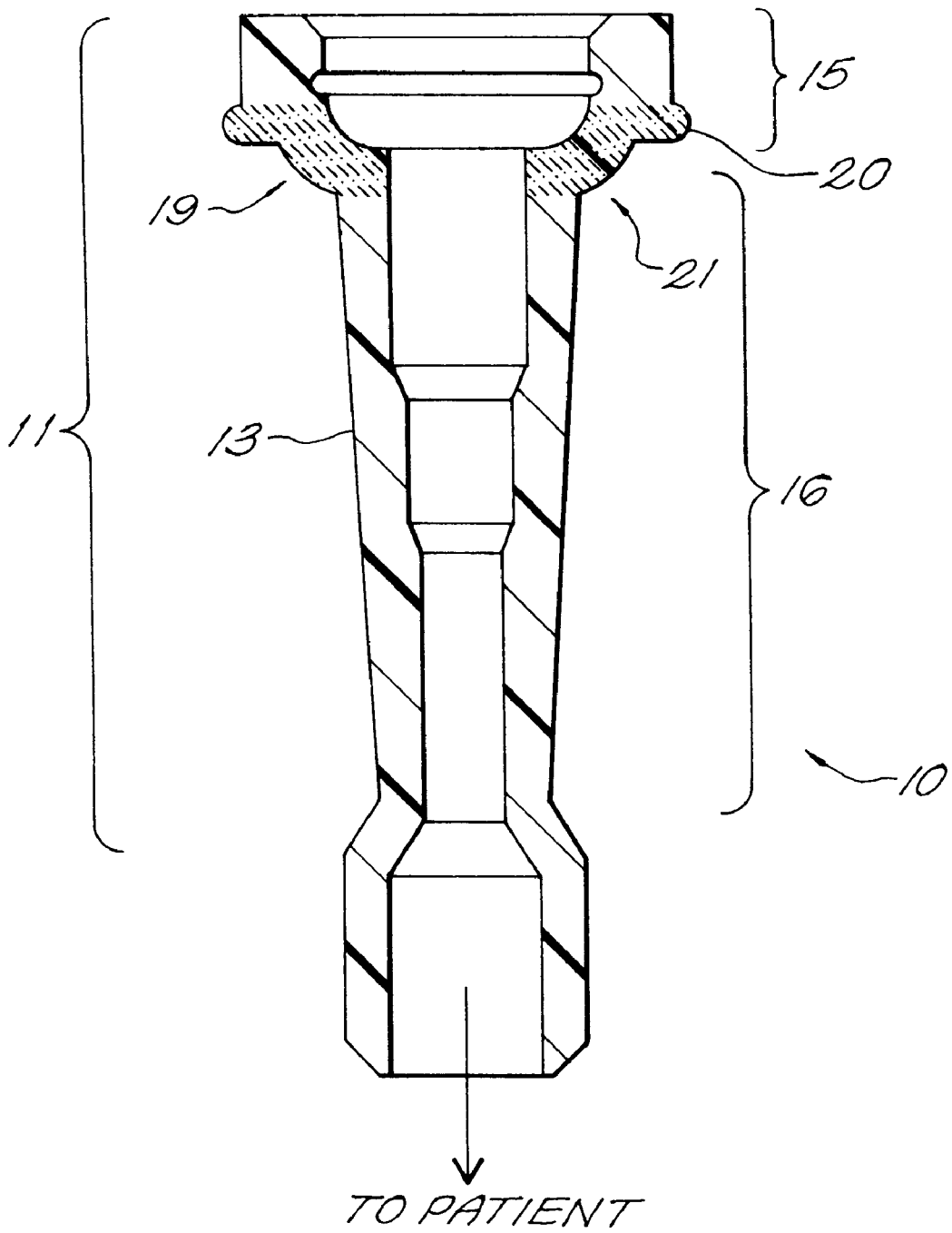
FIG. 3 shows a section view of the fluidic connector of FIG. 2 with the deformable buckling region highlighted.

Referring to FIG. 3, the deformable buckling region 19, the highlighted region of FIG. 3 that overlays a zone that partially includes both the first and second portions 15, 16 of the tube connection site 11 where the two portions 15, 16 join. Specifically, the deformable buckling region 19 is the area beginning at an outer annular ridge 20 and ending where a curved portion 21 of the tube connection site 11 terminates. The outer annular ridge 20 serves to maintain the radial dimensional integrity of the first larger diameter portion 15 and provides termination of the buckling zone.

Figure 5:
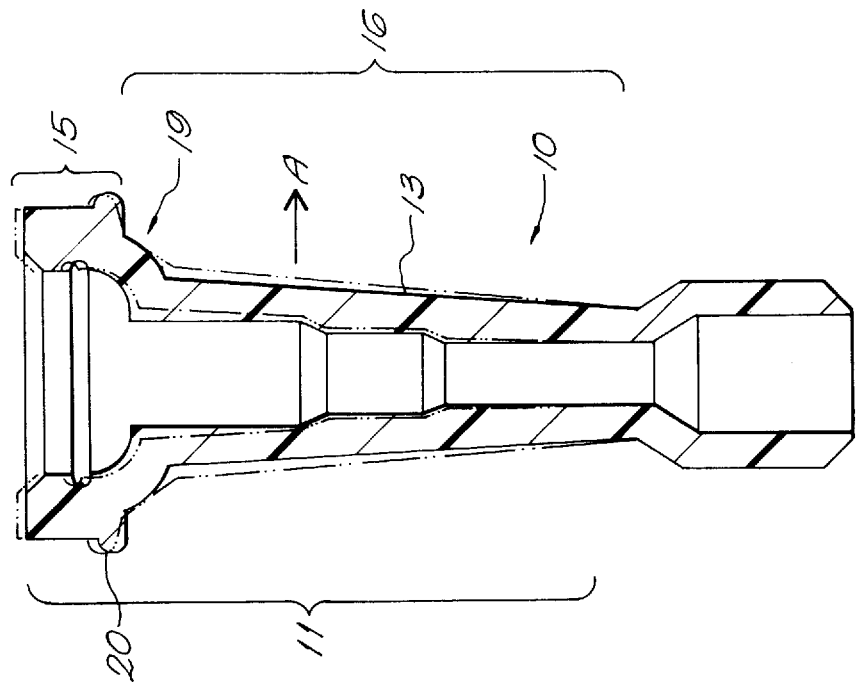
FIG. 5 is the connection site formed in accordance with the present invention showing in phantom how the deformable buckling region stretches in order to maintain the dimensional stability of the capping portion.
Figure 4:
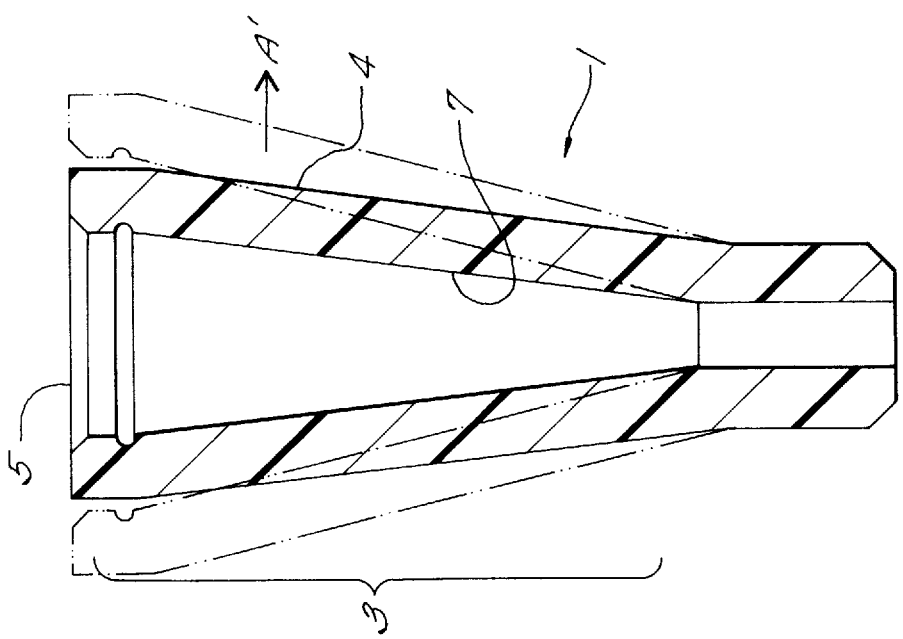
FIG. 4 is the prior art connection site of FIG. 1 showing in phantom how the connection site wall stretches out after prolonged insertion of a male adapter.

Referring to FIGS. 4 and 5, the operation of the deformable buckling region will be explained. As seen in FIG. 4, the original configuration of the prior art fluidic connector 1 before plastic deformation occurs is shown in solid while the configuration of that same connector 1 after the sealing and plugging portion 7 have been stretched out is shown in phantom. Without the deformable buckling region 19, the entire length of the sealing and plugging portion 7 is subject to stretching out. Leakage occurs when the opening 5 is plugged because the same surface is used to both plug the tube connection site 3 as well as to form a seal against the male adapter. Thus, when a nonconforming male adapter is inserted into the tube connection site 3 for a prolonged period, the entire length of the sealing and plugging portion 7 is stretched out permanently in a radial direction, denoted as direction A' in FIG. 4. This radial displacement of the wall 4 creates a larger diameter aperture at the opening 5. Radial displacement of opening 5 also results in an attendant loss of axial retention force when a plug is used to seal off the tube connection site 3 since the plug no longer securely fits the opening 5.

Referring to FIG. 5, the fluidic connector 10 of the present invention is shown. The original configuration of the fluidic connector 10 before insertion of a male adapter into the smaller diameter portion 16 is shown in solid, while the configuration of the connector 10 after plastic deformation has occurred is shown in phantom. When the tube connection site 11 is subjected to plastic deformation, the second, smaller diameter portion 16 is stretched radially or in the A direction, the deformable buckling region 19 deforms, with the deformation terminating at the outer annular ridge 20 and possibly resulting in translation of the first, larger diameter portion 15 axially without affecting the size and shape of the larger diameter portion 15 with respect to its plugging function.

Figure 6:
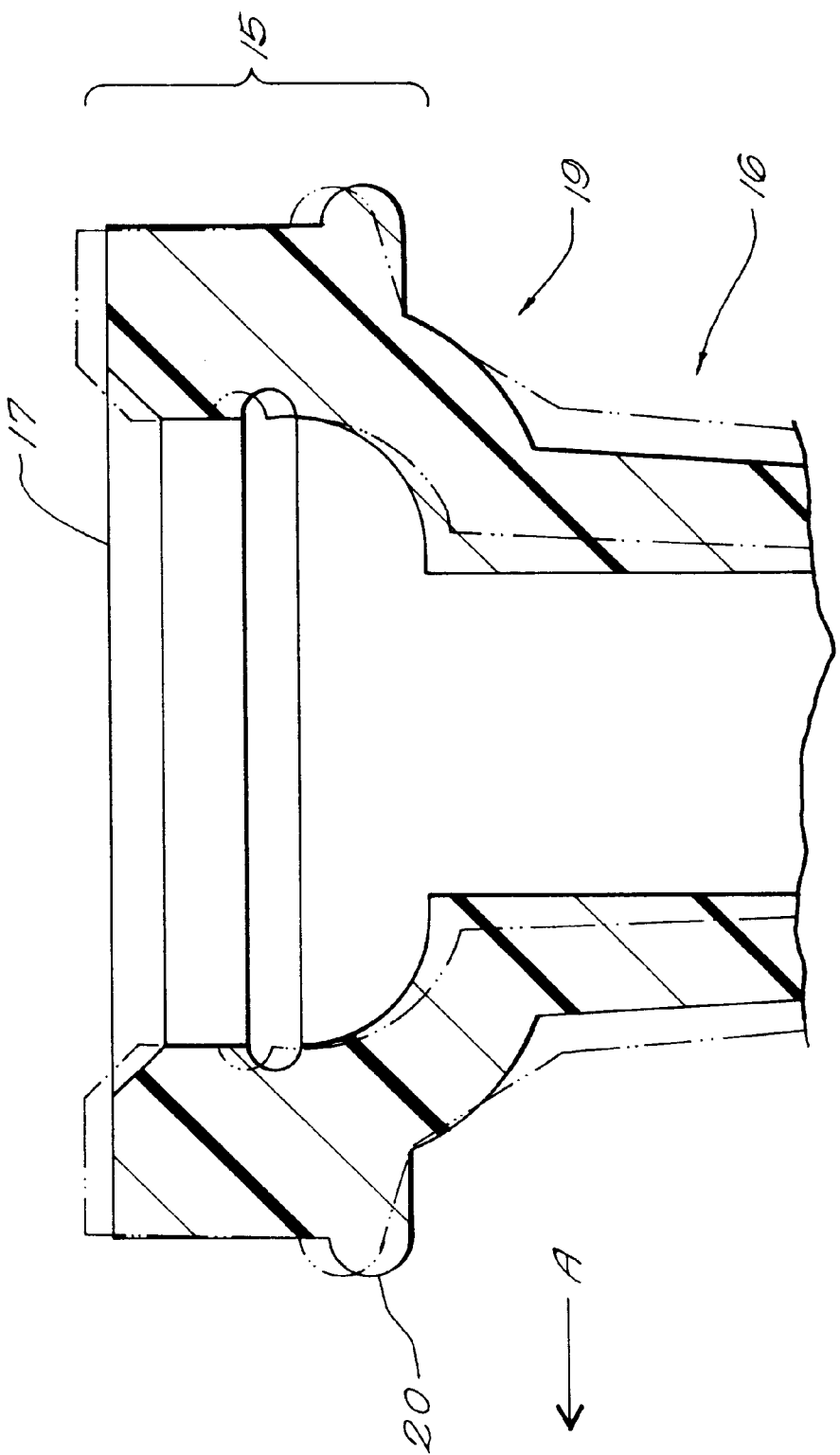
FIG. 6 is a partial view of the connection site formed in accordance with the present invention showing how the original dimensions of the deformable buckling region stretch in phantom.

Referring to FIG. 6, an enlarged view of the fluidic connector 10 with the deformable buckling region 19 is shown. In the preferred embodiment, a male connector (not shown) is inserted into the second, smaller diameter portion 16, expanding portion 16 radially in the A direction. However, the buckling or unwrapping effect of the deformable buckling region 19 allows the portion of the first, larger diameter portion 15 that is adjacent to the deformable buckling region 19 to be isolated from forces that would expand it radially, even in the absence of an outer annular ridge 20. However, the addition of one or more annular ridges 20 will further isolate the first, larger diameter portion 15 from any forces which might expand it radially. The axial component of the deformation of the deformable buckling region 19 can result in a change in the overall length of the first, larger diameter portion 15, either longer or shorter, depending on the specific configuration of the deformable buckling region 19. The net effect of this change in length, which is shown in phantom in FIG. 6, is an axial translation of the first larger diameter portion 15 relative to the rest of the connection site. 11.

Figure 7:
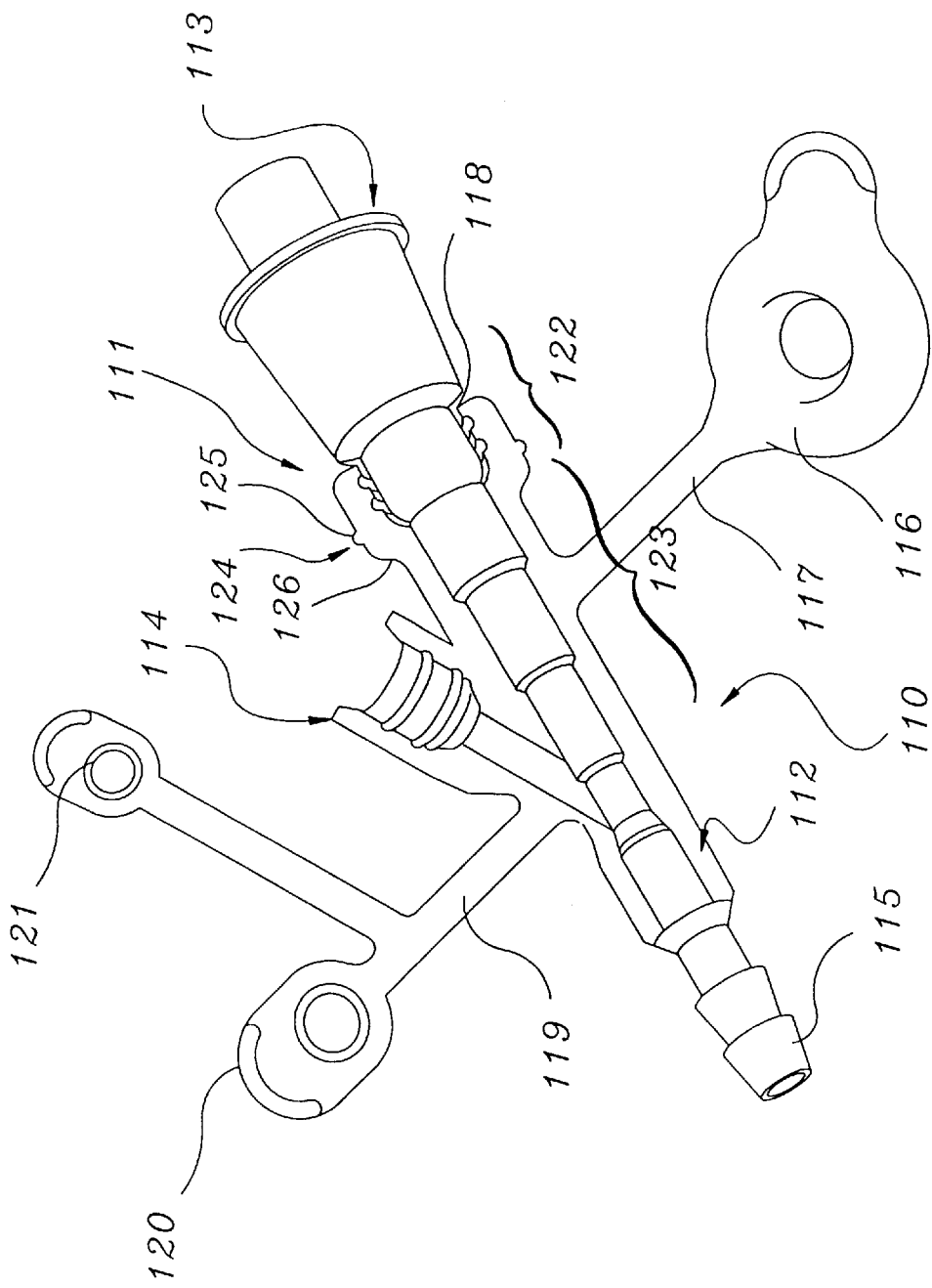
FIG. 7 is a section view of a fluidic connector showing the preferred embodiment of the connection site formed in accordance with the present invention.

Referring to FIG. 7, the preferred embodiment of the present invention is shown. The preferred embodiment consists of a Y-Site connector 110 comprising a tube connection site 111 at the proximal end of connector 110, a patient connection site 112 at the distal end of connector 110, and a flushing port 114 at the midpoint along connector 110 which is set at an angle in relation to the tube connection site 111. Further, the tube connection site 111 has a male adapter 113 inserted therein for connection to a lumen (not shown) while the patient connection site 112 is adapted to receive a barbed connector 115 for attachment to a lumen (not shown) leading to a patient. The Y-Site connector 110 also includes a cap 116 tethered to the tube connection site 111 by an arm member 117 and is used to plug the opening 118. Finally, a luer taper adapter 120 in combination with a flushing port cap 121 is tethered to the flushing port 114 by a flushing port arm member 119. The tube connection site 111 further includes a first, larger diameter portion 122 and a second, smaller diameter portion 123 with a deformable buckling region 124 overlaying parts of both portions 122, 123 where portions 122, 123 join. The deformable buckling region 124 includes an outer annular ridge 125 and a curved portion 126 and functions in the same manner as explained above by acting as a buffer for the first larger diameter portion 122.

Figure 8:
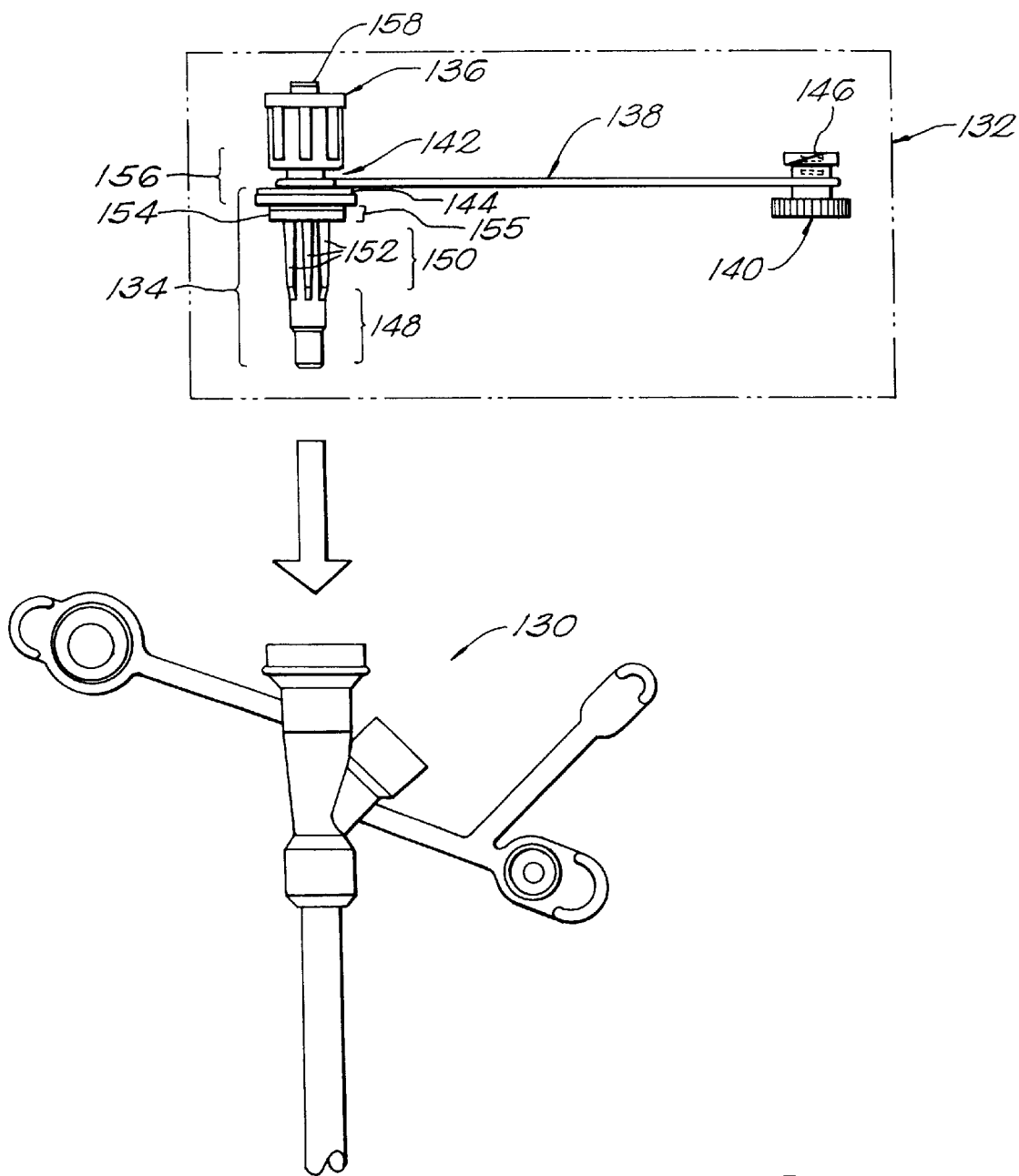
FIG. 8 is a plan view, partly in cross-section, as indicated by the dashed lines, of the European luer adapter and the fluidic connector.

Referring to FIG. 8, a fluidic connector is shown generally at 130. Fluidic connector 130 is preferably identical to or similar to fluidic connector 10 or Y-site connector 110. Above fluidic connector 130 is a luer adapter shown generally at 132.

Luer adapter 132 comprises male-to-male luer 134, optional luer skirt 136 disposed on male-to-male luer 134, tether 138 disposed at one end on male-to-male luer 134, and luer cap 140 disposed at the other end of tether 138. Optional luer skirt 136 has internal threads (not shown) and is disposed on a hub portion 142 of male-to-male luer 134 and retained by enlarged portions 144 (only one side shown) of male-to-male luer 134. One end of tether 138 is also disposed on a hub portion 142 of male-to-male luer 134. The other end of tether 138 retains luer cap 140. Luer cap 140 has an external thread 146 which is adapted to engage the internal threads of luer skirt 136. Male-to-male luer 134 itself is made from and has a graduated tube portion 148, a rib portion 150 wherein a plurality of gripping ribs 152 are provided to assist in providing a reliable connection with fluidic connector 130, a flange 154, an assembly-retaining area 156, and a male connector 158 for connecting to a female source.

Figure 9:
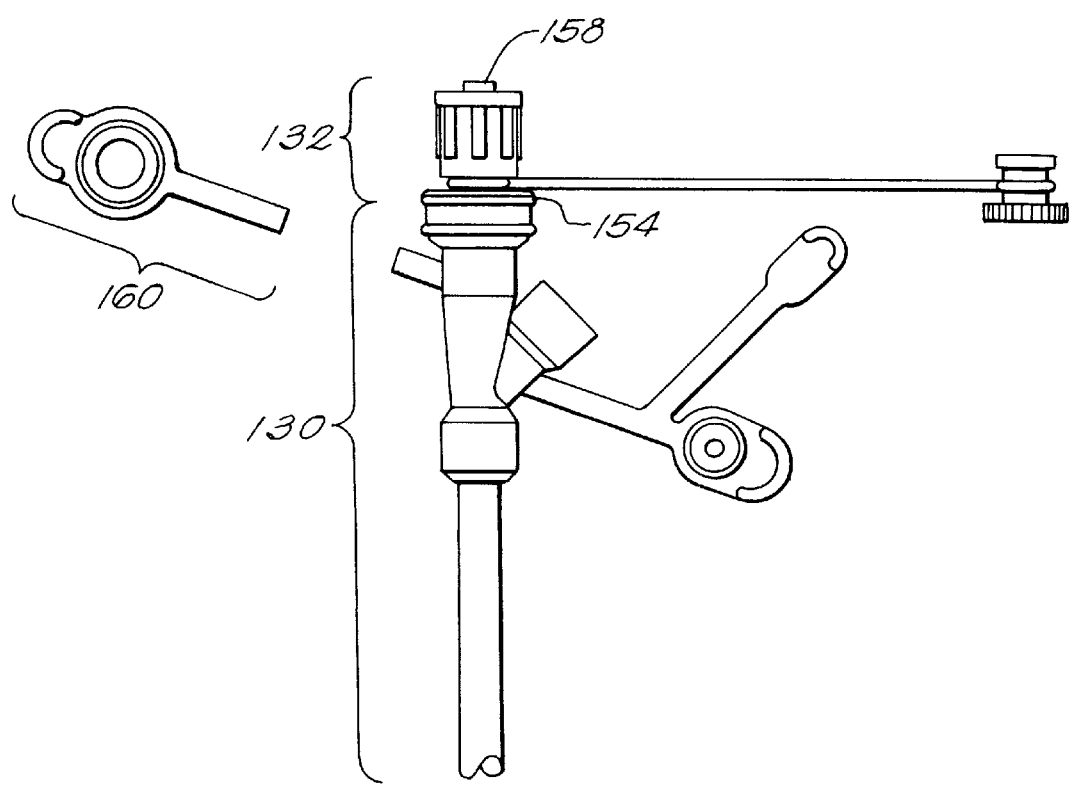
FIG. 9 is a plan view of the European luer adapter as inserted into the fluidic connector.

Referring to FIG. 9, luer adapter 132 is shown fully inserted into fluidic connector 130. In operation, luer adapter 132 is inserted into fluidic connector 130 to permit male connector 158 to be presented to a female source (not shown). The interior of fluidic connector 130 is internally graduated to accommodate various sizes of male connectors. Graduated tube portion 148 of luer adapter 132 as shown in FIG. 8 has two different diameter portions adapted to the internal graduations in fluidic connector 130 to provide a reliable seal between the adapter 132 and the connector 130. When luer adapter 132 is fully inserted into fluidic connector 130, a plurality of ribs 152 present an increasing outer diameter to meet the internally graduated fluidic connector 130. The plurality of ribs 152 are adapted to present a noncontinuous circular surface area of contact to the interior of fluidic connector 130. The surface area presented helps prevent creep or plastic deformation in fluidic connector 130, but is adequate to permit a reliable friction fit. It is also preferred that a redundant seal system which prevents fluid leakage or introduction of foreign matter into adapter 132 is preferred. Accordingly, flange 154 of luer adapter 132 provides a function similar to a cap to seal the unfilled remainder of the opening of fluidic connector 130 and held in place by friction fit between the inner portion of the opening of fluidic connector 130 and a downwardly extending cylindrical portion 155 of flange 154. Once sealed, a cap portion 160 for closing the opening of fluidic connector may be cut off or otherwise removed.

Initial results obtained in accordance with the present invention show that all adapters tested above 172,250 Pa (25 psi) over a thirty day pressure leak test, which exceeds by over three times the test specification requirement of 55,120 Pa (8 psi). In addition, the pull force required to remove the luer adapter 132 from fluidic connector 130 ranged from above 4.54 kg to 6.81 kg (10 pounds to 15 pounds) on average, which surpasses the typical pull force requirement of 5 pounds for a solvent bonded connection in Dobhoff feeding tubes.

Although particular embodiments of the invention have been shown, it is not intended that the invention be limited thereby, instead the scope of the present invention is intended to be limited by the appended claims.

I claim:

1. A connection site for a fluidic connector, said connection site having an inner portion, the connection site comprising:
   a first diameter portion;
   a second diameter portion having an external diameter and a plurality of different size diameter segments, said second diameter portion adjacent to said first diameter portion, said first diameter portion having a larger diameter than said second diameter portion, said first diameter portion retaining the same shape when said external diameter of said second diameter portion is increased.

2. The connection site according to claim 1, wherein a deformable region forms a part of said first and second diameter portions, wherein said deformable region deforms in such a manner that when said second diameter portion stretches in a radial direction said first diameter portion retains the same diameter.

3. The connection site according to claim 2, wherein the deformable region further includes one or more outer ridges and a curved portion, the curved portion stretches in such a manner that the outer ridges translate axially and contribute to the termination of the deformation.

4. The connection site according to claim 1, wherein the first diameter portion retains its original diameter when said deformable region is subjected to a radial force and displacement exerted from the inner portion of said fluidic connector.

5. The connection site according to claim 1, wherein the force exerted from within said fluidic connector originates from an adapter inserted into said connection site, said adapter exerting a radial force against said inner portion.

6. The connection site according to claim 1, wherein the second diameter portion is adapted to receive a variety of different size adapters therein.

7. A connection site for a fluidic connector according to claim 1, further comprising:
   a luer adapter having a graduated tube portion, a rib portion wherein a plurality of gripping ribs are provided to assist in providing a reliable connection with a fluidic connector, a sealing flange, an assembly-retaining area, and a connector for connecting to a source.

8. A connection site for a fluidic connector according to claim 7, further comprising:
   a luer skirt disposed on said luer adapter at said assembly-retaining area;
   a tether having a first end and a second end, said first end of said tether being connected to said luer adapter at said assembly-retaining area; and
   a luer cap connected to said second end of said tether adapted to removably attach to said adapter.

9. A connection site for a fluidic connector according to claim 7, wherein said flange of said adapter is provided with a cylindrical portion, said flange being adapted to form a redundant seal against leakage when said adapter is inserted into said fluidic connector.

10. A connection site for a fluidic connector, said connection site having an inner portion, the connection site comprising:
    a first diameter portion;
    a second diameter portion having a plurality of different size diameter segments, said second diameter portion adjacent to said first diameter portion, said first diameter portion having a larger diameter than said second diameter portion,
    a deformable region forming a part of said first and second diameter portions where said first and second diameter portions are adjacent, wherein said deformable region buckles in such a manner that when said second diameter portion stretches in a radial direction said first diameter portion translates axially.

11. The connection site according to claim 10, wherein the deformable region further includes an outer ridge and curved portion, the curved portion stretching in such a manner that the outer ridge moves axially.

12. The connection site according to claim 10, wherein the first diameter portion retains its original diameter when said deformable region is subjected to a radial force exerted from said second diameter portion.

13. The connection site according to claim 10, wherein the force exerted from within said fluidic connector originates from an adapter inserted into said connection site, said adapter exerting a radial force against said second diameter portion.

14. The connection site according to claim 10, wherein the second diameter portion is adapted to receive a variety of different size adapters therein.

15. A connection site for a fluidic connector according to claim 10, further comprising:
    a luer adapter having a graduated tube portion, a rib portion wherein a plurality of gripping ribs are provided to assist in providing a reliable connection with a fluidic connector, a sealing flange, an assembly-retaining area, and a connector for connecting to a source.

16. A connection site for a fluidic connector according to claim 15, wherein said flange of said adapter is provided with a cylindrical portion, said flange being adapted to form a redundant seal against leakage when said adapter is inserted into said fluidic connector.

17. A connection site for a fluidic connector according to claim 15, further comprising:
    a luer skirt disposed on said luer adapter at said assembly-retaining area;
    a tether having a first end and a second end, said first end of said tether being connected to said luer adapter as said assembly-retaining area; and
    a luer cap connected to said second end of said tether adapted to removably attach to said connector.

18. A connection site for a fluidic connector, said connection site having an inner portion, the connection site comprising:
    a first diameter portion;
    a second diameter portion having a plurality of different size diameter segments, said second diameter portion adjacent to said first diameter portion, said first diameter portion having a larger diameter than said second diameter portion, a deformable region forms a part of said first and second diameter portions where said first and second diameter portions are adjacent, wherein said deformable region buckles in such a manner that the first diameter portion stretches axially and said second diameter portion stretches in a radial direction, said first diameter portion retaining its original diameter when said deformable region buckles.

19. The connection site according to claim 18, wherein the deformable region further includes an outer ridge and curved portion, the curved portion stretching due to the radial force in such a manner that the outer ridge stretches axially.

20. The connection site according to claim 18, wherein the force exerted from within said fluidic connector originates from an adapter inserted into said connection site, said adapter exerting a radial force against said second diameter portion.

21. The connection site according to claim 18, wherein the second smaller diameter portion is adapted to receive a variety of different size adapters therein.

22. A connection site for a fluidic connector according to claim 18, further comprising:

a luer adapter having a graduated tube portion, a rib portion wherein a plurality of gripping ribs are provided to assist in providing a reliable connection with a fluidic connector, a sealing flange, an assembly-retaining area, and a connector for connecting to a source.

23. A connection site for a fluidic connector according to claim 22, further comprising:

a luer skirt disposed on said luer adapter at said assembly-retaining area;

a tether having a first end and a second end, said first end of said tether being connected to said luer adapter at said assembly-retaining area; and a luer cap connected to said second end of said tether adapted to removably attach to said connector.

24. A connection site for a fluidic connector according to claim 22, wherein said flange of said adapter is provided with a cylindrical portion, said flange being adapted to form a redundant seal against leakage when said adapter is inserted into said fluidic connector.

* * * * *

UNITED STATES PATENT AND TRADEMARK OFFICE
CERTIFICATE OF CORRECTION

PATENT NO. : 5,988,700
DATED      : November 23, 1999
INVENTOR(S): Prichard

It is certified that error appears in the above-identified patent and that said Letters Patent are hereby corrected as shown below:

At Column 1, line 56:

The word, "synonomously" should be changed to --synonymously--.

Signed and Sealed this

Fourteenth Day of November, 2000

Attest:

Q. TODD DICKINSON

*Attesting Officer*                    *Director of Patents and Trademarks*